(12) United States Patent
Lanini et al.

(10) Patent No.: US 7,314,979 B2
(45) Date of Patent: Jan. 1, 2008

(54) MULTIBRANCHING WATERMELON PLANT AND METHOD OF PRODUCING

(75) Inventors: Brenda Lanini, Davis, CA (US); Theodore H. Superak, Davis, CA (US); Bill Copes, Sacramento, CA (US)

(73) Assignee: Harris Moran Seed Company, Modesto, CA (US)

( * ) Notice: Subject to any disclaimer, the term of this patent is extended or adjusted under 35 U.S.C. 154(b) by 208 days.

(21) Appl. No.: 10/999,650

(22) Filed: Nov. 30, 2004

(65) Prior Publication Data

US 2006/0117417 A1    Jun. 1, 2006

(51) Int. Cl.
*A01H 5/00*   (2006.01)
*A01H 5/10*   (2006.01)
*A01H 4/00*   (2006.01)
*A01H 1/02*   (2006.01)
*C12N 15/82*  (2006.01)

(52) U.S. Cl. .................... 800/308; 800/260; 435/410

(58) Field of Classification Search ............... 800/260, 800/266, 268, 269, 308; 435/410
See application file for complete search history.

(56) References Cited

U.S. PATENT DOCUMENTS

| | | | | |
|---|---|---|---|---|
| 5,304,719 | A | * | 4/1994 | Segebart ............... 800/303 |
| 5,367,109 | A | * | 11/1994 | Segebart ............... 800/320.1 |
| 5,763,755 | A | * | 6/1998 | Carlone ............... 800/320.1 |
| 5,777,196 | A | | 7/1998 | Hall |
| 5,850,009 | A | * | 12/1998 | Kevern ............... 800/271 |
| 5,948,957 | A | | 9/1999 | Chapko et al. |
| 5,969,212 | A | | 10/1999 | Getschman |
| 6,747,191 | B2 | * | 6/2004 | Zhang ............... 800/308 |

FOREIGN PATENT DOCUMENTS

| | | |
|---|---|---|
| WO | WO 00/70933 A1 | 11/2000 |
| WO | WO 03/051103 A2 | 6/2003 |
| WO | WO 03/056901 A2 | 7/2003 |
| WO | WO 03/075641 A2 | 9/2003 |
| WO | WO 03/096798 A1 | 11/2003 |

OTHER PUBLICATIONS

Poehlman, J.M. and D.A. Sleper. 1995. Breeding Field Crops. 4th ed. Iowa State University Press, Ames, Iowa, p. 473.*
Adelberg, J.W., et al., 1994. Explant origin affects the frequency of tetraploid plants from tissue culture of melon. HortScience 29(6):689-692.
Bennetzen, et al., 1992. Approaches and progress in the molecular cloning of plant disease resistance genes, In Genetic Engeneering. 14:99-124, Ed. J.K. Setlow, Plenum Press, NY.
DeBolle, et al., 1996. Antimicrobial peptides from *Mirabilis jalapa* and *Amaranthus candatus*: expression, processing, localization and biological activity in transgenic tobacco. Plant Molec. Biol. 31:993-1008.
Ezura, et al., 1994. Ploidy of somatic embryos and the ability to regenerate plantlets in melons (*Cucumis melo* L.). Plant Cell Reports 14:107-111.
Kraft, et al., 2000. Linkage disequilibrium and fingerprinting in sugar beet. Theor. Appl. Genet. 101:323-326.
Pang, et al., 1992. Expression of a gene encoding a scorpion insectotoxin peptide in yeast, bacteria and plants. Gene 116:165-172.
Zhang, et al., 1996. Development of genic male-sterile watermelon lines with delayed-green seedling marker. HortScience 31(1):123-126.
Mohr, H.C., et al., 1975. Inheritance and Morphological Traits of a Double Recessive Dwarf in Watermelon, *Citrullus lanatus* (Thunb.) Mansf. J. Amer. Soc. Hort. Sci. 100(2):135-137.

* cited by examiner

*Primary Examiner*—David H. Kruse
*Assistant Examiner*—Keith O. Robinson
(74) *Attorney, Agent, or Firm*—Jondle & Associates, P.C.

(57) ABSTRACT

The present invention relates to a watermelon plant, seed, variety and hybrid. More specifically, the invention relates to a watermelon plant having an allele which results in a multibranching compact watermelon plant with small fruit. The invention also relates to crossing inbreds, varieties and hybrids containing the allele to produce novel types and varieties of watermelon plants.

16 Claims, No Drawings

MULTIBRANCHING WATERMELON PLANT AND METHOD OF PRODUCING

FIELD OF THE INVENTION

The present invention relates to an allele of watermelon designated "HMBN", which results in multibranching compact plants and small fruit. The present invention also relates to a watermelon seed, a watermelon plant and parts of a watermelon plant, a watermelon variety and a watermelon hybrid which comprise the mutant allele. In addition, the present invention is directed to transferring the HMBN allele in the watermelon plant to other watermelon varieties and species and is useful for producing new types and varieties of multibranching watermelon.

BACKGROUND OF THE INVENTION

The present invention relates to a new and distinctive watermelon mutant allele, designated "HMBN". There are numerous steps in the development of any novel, desirable plant germplasm. Plant breeding begins with the analysis and definition of problems and weaknesses of the current germplasm, the establishment of program goals, and the definition of specific breeding objectives. The next step is selection of germplasm that possess the traits to meet the program goals. The goal is to combine in a single variety or hybrid an improved combination of desirable traits from the parental germplasm. These important traits may include higher yield, field performance, fruit and agronomic quality such as firmness, color, content in soluble solids, acidity and viscosity, resistance to diseases and insects, and tolerance to drought and heat.

All cultivated forms of watermelon belong to the polymorphic species *Citrullus lanatus* that is grown for its edible fruit that weigh from five to forty pounds, depending on variety. As a crop, watermelons are grown commercially wherever environmental conditions permit the production of an economically viable yield. In the United States, the main watermelon production areas are Florida, Georgia, Texas and California. Fresh watermelon are eaten sliced or diced and may also be used as an ingredient in prepared foods.

Watermelon is thought to have originated in southern Africa because it is found growing wild throughout the area, and reaches maximum diversity of forms there. It has been cultivated in Africa for over 4,000 years. *Citrullus colocynthis* is considered to be a wild ancestor of watermelon. It has fruit that are small, with a maximum diameter of 75 mm, with bitter flesh and small, brown seeds. Although *Citrullus* species grow wild in southern and central Africa, *C. colocynthis* also grows wild in India. Cultivation of watermelon began in ancient Egypt and India and is thought to have spread from those countries through the Mediterranean, Near East, and Asia. The crop has been grown in the Untied States since 1629.

*Citrullus lanatus* is a member of the family Cucurbitaceae which consists of about 90 genera and 700 to 760 species, mostly of the tropics. The family includes pumpkins, squashes, gourds, watermelon, loofah, and several weeds. There are four recognized *Citrullus* species, *C. lanatus, C. colocynthis, C. rehmii* and *C. ecirrhosus*; all have 22 chromosomes and can be crossed with each other successfully.

*C. lanatus* is an annual watermelon. It has large, broad green leaves, which are orbicular to triangular-ovate in shape and deeply three to five lobed or sometimes simple. Medium-sized flowers are monoecious and have short pedicels. Fruits are of medium to large size, with thick rind and solid flesh with high water content. Flesh color may be red, yellow, or white. Seeds are ovate to oblong, are strongly compressed and have white or brown seed coats. The root system of the plant is a deep, spreading fibrous semi-taproot system that extends six feet or more below the soil surface.

*C. colocynthis* is a perennial watermelon. It differs from *C. lanatus* primarily in the size of plant organs. Leaves are small with narrow lobes, and are hairy and grayish in color. Flowers are monoecious and small. Bloom is profuse in autumn, when fresh vegetative growth also occurs. Seeds are small and brown. Fruits are small, not exceeding 3 inches in diameter, with rind and spongy flesh that are always bitter.

*C. ecirrhosus* is a perennial watermelon. *C. ecirrhosus* closely resembles *C. colocynthis* in vegetative characteristics, but its leaves are more divided, are covered with dense fine hairs, and have strongly recurved margins. Tendrils are lacking. Fruits are subglobose with white flesh and are bitter like *C. colocynthis*. Flowers are not produced until the second year of growth.

Commercial watermelon plants are monoecious, producing both male and female flowers. A female flower can be easily recognized by the swelling of its base that resembles a tiny watermelon. Honeybees, mainly in the morning, pollinate the flowers. There are many diverse cultivars for production with varieties having dark green to yellow rind coloring, striped or solid coloring, and containing seeds or are seedless. The shape of the fruit varies from round to elliptical.

Watermelon varieties fall into three broad classes based on how the seed was developed: open-pollinated, $F_1$ hybrid and triploid (commonly referred to as seedless). Open-pollinated varieties are developed through several generations of selection. The selection can be based upon yield, quality characteristics and disease resistance. $F_1$ hybrids are developed from two inbred lines that have been selfed for several generations and then crossed. $F_1$ hybrid seed exhibit increased uniformity of type and time of harvest compared with open-pollinated seed and can exhibit as much as a 20 percent to 40 percent increase in yields over open-pollinated varieties grown under similar conditions. The third type is triploid or seedless watermelon. These are developed by creating watermelon plants with double the usual chromosome number and crossing them with normal watermelon plants. The resulting plants have one-and-a-half times the normal chromosome number. Because they have an odd number of chromosomes, they cannot form viable seed. Although triploid watermelons are referred to as seedless, they are not truly seedless but rather have undeveloped seeds that are soft and edible.

Choice of breeding or selection methods depends on the mode of plant reproduction, the heritability of the trait(s) being improved, and the type of cultivar used commercially (e.g., $F_1$ hybrid cultivar, pureline cultivar, etc.). For highly heritable traits, a choice of superior individual plants evaluated at a single location will be effective, whereas for traits with low heritability, selection should be based on mean values obtained from replicated evaluations of families of related plants. Popular selection methods commonly include pedigree selection, modified pedigree selection, mass selection, and recurrent selection.

The complexity of inheritance influences choice of the breeding method. Backcross breeding is used to transfer one or a few favorable genes for a highly heritable trait into a desirable cultivar. This approach has been used extensively for breeding disease-resistant cultivars. Various recurrent selection techniques are used to improve quantitatively inherited traits controlled by numerous genes. The use of recurrent selection in self-pollinating crops depends on the ease of pollination, the frequency of successful hybrids from each pollination, and the number of hybrid offspring from each successful cross.

Each breeding program should include a periodic, objective evaluation of the efficiency of the breeding procedure. Evaluation criteria vary depending on the goal and objectives, but should include gain from selection per year based on comparisons to an appropriate standard, overall value of the advanced breeding lines, and number of successful cultivars produced per unit of input (e.g., per year, per dollar expended, etc.).

Promising advanced breeding lines are thoroughly tested and compared to appropriate standards in environments representative of the commercial target area(s) for three years at least. The best lines are candidates for new commercial cultivars; those still deficient in a few traits are used as parents to produce new populations for further selection.

These processes, which lead to the final step of marketing and distribution, usually take from eight to 12 years from the time the first cross is made. Therefore, development of new cultivars is a time-consuming process that requires precise forward planning, efficient use of resources, and a minimum of changes in direction.

A most difficult task is the identification of individuals that are genetically superior, because for most traits the true genotypic value is masked by other confounding plant traits or environmental factors. One method of identifying a superior plant is to observe its performance relative to other experimental plants and to a widely grown standard cultivar. If a single observation is inconclusive, replicated observations provide a better estimate of its genetic worth.

The goal of watermelon plant breeding is to develop new, unique and superior watermelon inbreds and hybrids. The breeder initially selects and crosses two or more parental lines, followed by repeated selfing and selection, producing many new genetic combinations. The breeder can theoretically generate billions of different genetic combinations via crossing, selfing and mutations. The breeder has no direct control at the cellular level. Therefore, two breeders will never develop the same line, or even very similar lines, having the same watermelon traits.

Each year, the plant breeder selects the germplasm to advance to the next generation. This germplasm is grown under unique and different geographical, climatic and soil conditions, and further selections are then made, during and at the end of the growing season. The varieties which are developed are unpredictable. This unpredictability is because the breeder's selection occurs in unique environments, with no control at the DNA level (using conventional breeding procedures), and with millions of different possible genetic combinations being generated. A breeder of ordinary skill in the art cannot predict the final resulting lines he develops, except possibly in a very gross and general fashion. The same breeder cannot produce the same line twice by using the exact same original parents and the same selection techniques. This unpredictability results in the expenditure of large research monies to develop superior new watermelon varieties.

The development of commercial watermelon hybrids requires the development of homozygous inbred lines, the crossing of these lines, and the evaluation of the crosses. Pedigree, backcross or recurrent selection breeding methods are used to develop lines from breeding populations. Breeding programs combine desirable traits from two or more lines or various broad-based sources into breeding pools from which mutant alleles are developed by selfing and selection of desired phenotypes. The new inbreds are crossed with other inbred lines and the hybrids from these crosses are evaluated to determine which have commercial potential.

Pedigree breeding is used commonly for the improvement of self-pollinating crops or inbred parents of cross-pollinating crops. Two parents which possess favorable, complementary traits are crossed to produce an $F_1$. An $F_2$ population is produced by selfing one or several $F_1$'s or by intercrossing two $F_1$'s (sib mating). Selection of the best individuals is usually begun in the $F_2$ population; then, beginning in the $F_3$, the best individuals in the best families are selected. Replicated testing of families, or hybrid combinations involving individuals of these families, often follows in the $F_4$ generation to improve the effectiveness of selection for traits with low heritability. At an advanced stage of inbreeding (i.e., $F_6$ and $F_7$), the best lines or mixtures of phenotypically similar lines are tested for potential release as new cultivars or new parents for hybrids.

Mass and recurrent selections can be used to improve populations of either self- or cross-pollinating crops. A genetically variable population of heterozygous individuals is either identified or created by intercrossing several different parents. The best plants are selected based on individual superiority, outstanding progeny, or excellent combining ability. The selected plants are intercrossed to produce a new population in which further cycles of selection are continued.

Backcross breeding has been used to transfer genes for a simply inherited, highly heritable trait into a desirable homozygous cultivar or inbred which is the recurrent parent. The source of the trait to be transferred is called the donor parent. The resulting plant is expected to have the attributes of the recurrent parent (e.g., cultivar) and the desirable trait transferred from the donor parent. After the initial cross, individuals possessing the phenotype of the donor parent are selected and repeatedly crossed (backcrossed) to the recurrent parent. The resulting plant is expected to have the attributes of the recurrent parent (e.g., cultivar) and the desirable trait transferred from the donor parent.

Descriptions of other breeding methods that are commonly used for different traits and crops can be found in one of several reference books (e.g., Principles of Plant Breeding, John Wiley and Son, pp.115-161,1960; Allard, 1960; Simmonds, 1979; Sneep et al., 1979; Fehr, 1987).

Proper testing should detect any major faults and establish the level of superiority or improvement over current cultivars. In addition to showing superior performance, there must be a demand for a new cultivar that is compatible with industry standards or which creates a new market. The introduction of a new cultivar will incur additional costs to the seed producer, the grower, processor and consumer; for special advertising and marketing, altered seed and commercial production practices, and new product utilization. The testing preceding release of a new cultivar should take into consideration research and development costs as well as technical superiority of the final cultivar. For seed-propagated cultivars, it must be feasible to produce seed easily and economically.

Once the inbreds that give the best hybrid performance have been identified, the hybrid seed can be reproduced indefinitely as long as the homogeneity of the inbred parent is maintained. A single-cross hybrid is produced when two inbreds are crossed to produce the $F_1$ progeny.

Watermelon has been improved by domestication and formal plant breeding from a late maturing vine with small fruit having hard, white flesh and bland or bitter taste, into an early maturing, more compact plant with large fruit having edible, sweet flesh. In the last century, plant breeders working in public or private programs in the United States and around the world have released varieties having disease resistance, dwarf vines, larger fruit, higher sugar content, higher lycopene content, seedlessness, and new flesh colors, such as dark red, orange and yellow. Recent advances in the breeding of seedless triploid hybrids have resulted in renewed popularity of watermelons, and per capita consumption has increased 37% since 1980.

However, even with such a tremendous diversity, most watermelon plants are large and produce large fruits weighing from five to forty pounds while there is an increasing demand for smaller plants and fruits. Some smaller plants have been discovered and a gene, dw-1, resulting in a dwarf plant habit has been identified as a single recessive gene (Mohr, H. C., Proc. Assoc. Southern Agric. Work., 53:174 (1956)). Another single recessive dwarfing gene, dw-2, which controls multibranching from the crown of the plant was identified in 1975 (Mohr, H. C. and M. S. Sandhu, J. Am. Soc. Hortic. Sci. 100:135-137).

These dwarfing genes apply only to the plant and not to the fruit resulting in large fruit on small plants. It has been very difficult for watermelon breeders to develop small plants with small fruit and commercially acceptable yield. Unexpectedly, the HMBN allele of the present invention results in both small plants and smaller fruits with commercially acceptable yield.

SUMMARY OF THE INVENTION

The present invention provides a new allele derived from *Citrullus lanatus* that is phenotypically expressed by the formation of compact plants and smaller fruits when present in the homozygous state. This mutant allele has been determined to be a single, recessive gene. The invention further provides plants, seeds, fruits and other plant parts such as pollen and ovules containing the mutant allele.

The invention also provides methods for introducing the allele into plants by crossing a variety which lacks the mutant allele with a variety that has the allele, backcrossing the progeny with the variety which lacks the mutant allele, selfing the resulting generations and then selecting the plants exhibiting a compact plant and smaller fruit.

In another aspect, the invention provides a method for producing a hybrid *Citrullus lanatus* seed comprising crossing a first cultivar plant parent with a second cultivar plant parent and harvesting the resultant hybrid *Citrullus lanatus* seed, wherein both parents are cultivars containing the mutant allele. The hybrid seeds, plant and parts thereof produced by such method are also part of the invention.

Another aspect of the invention relates to any watermelon seed or plant having the mutant allele HMBN.

In another aspect, the present invention provides regenerable cells for use in tissue culture. The tissue culture will preferably be capable of regenerating plants having the physiological and morphological characteristics of the foregoing inbred watermelon plant, and of regenerating plants having substantially the same genotype as the foregoing inbred watermelon plant. Preferably, the regenerable cells in such tissue cultures will be embryos, protoplasts, meristematic cells, callus, pollen, leaves, anthers, stems, petioles, roots, root tips, fruits, seeds, flowers, cotyledons, hypocotyls or the like. Still further, the present invention provides watermelon plants regenerated from the tissue cultures of the invention.

DEFINITIONS

In the description and tables which follow, a number of terms are used. In order to provide a clear and consistent understanding of the specification and claims, including the scope to be given such terms, the following definitions are provided:

Allele. "Allele" is any of one or more alternative forms of a gene, all of which alleles relate to one trait or characteristic. In a diploid cell or organism, the two alleles of a given gene occupy corresponding loci on a pair of homologous chromosomes.

Backcrossing. Backcrossing is a process in which a breeder repeatedly crosses hybrid progeny back to one of the parents, for example, a first generation hybrid $F_1$ with one of the parental genotypes of the $F_1$ hybrid.

Average fruit length. "Average fruit length" means the average length in centimeters of all fruits harvested from one or more watermelon plants of a specific genotype.

Average fruit number. "Average fruit number" means the average number of fruit harvested from one or more watermelon plants of a specific genotype.

Average fruit weight. "Average fruit weight" means the average weight in kilograms of all fruits harvested from one or more watermelon plants of a specific genotype.

Average fruit width. "Average fruit width" means the average width in centimeters of all fruits harvested from one or more watermelon plants of a specific genotype.

Average internode length. "Average internode length" means the average length of the internodes of a watermelon plant of a specific genotype measured in centimeters.

Average length to width ratio (L/W Ratio). "Average length to width ratio (L/W ratio) means the average length to width ratio from all fruits harvested from one or more watermelon plants of a specific genotype.

Average length of longest branch. "Average length of longest branch" means the average length of the longest branch of the watermelon plant in centimeters as measured from the crown of the plant.

Average length of shortest branch. "Average length of shortest branch" means the average length of the shortest branch of the watermelon plant in centimeters as measured from the crown of the plant.

Average number of secondary branches at 30 cm. "Average number of secondary branches at 30 cm" means the average number of secondary branches measured at 30 centimeters from the crown of the watermelon plant of a specific genotype.

Average number of secondary branches at 90 cm. "Average number of secondary branches at 90 cm" means the average number of secondary branches measured at 90 centimeters from the crown of the watermelon plant of a specific genotype.

Diploid plants. "Diploid plants" means plants or transplants derived from planting diploid seeds or from micro propagation.

Essentially all the physiological and morphological characteristics. A plant having "essentially all the physiological and morphological characteristics" means a plant having the physiological and morphological characteristics, except for the characteristics derived from the converted gene.

Explosive rind. "Explosive rind" in watermelon is a trait where the rind is tender and can burst open when cut with a knife. The rind can also explode before the watermelon fruit reaches physiological maturity and results in unmarketable fruit.

Hollowheart. "Hollowheart" is the characteristic of separation of tissue within the endocarp which can be caused by rapid fruit growth and weak tissue. The presence of Hollowheart (or one variant which is placental detachment) is affected by environment, but can also be selected against in the development of inbred lines. The genetic control of this undesirable trait is not understood.

Lobed leaf. "Lobed leaf" means a leaf having two or more lobes.

Nonlobed leaf. "Nonlobed leaf" means a leaf that is not lobed.

Plant. "Plant" includes plant cells, plant protoplasts, plant cells of tissue culture from which watermelon plants can be regenerated, plant calli, plant clumps and plant cells that are intact in plants or parts of plants such as pollen, flowers, seed, leaves, stems, rind, flesh and the like.

Plant diameter. "Plant diameter" means the average length of plant measurements in inches.

Quantitative Trait Loci (QTL). "Quantitative trait loci (QTL)" refer to genetic loci that control to some degree numerically representable traits that are usually continuously distributed.

Regeneration. "Regeneration" refers to the development of a plant from tissue culture.

Rind pattern. The "rind pattern" is the coloration of the rind in watermelons which can vary from light green, often termed gray, to medium green to very dark green which appears to be almost black. In addition, the rind may have stripes of various designs which are typical of a variety or type. Therefore the terms 'tiger stripe', 'mottle stripe', 'dark mottle stripe', etc. are used to identify various patterns.

Seedless. "Seedless" means a watermelon fruit in which the embryo development is aborted and the seed development process has stopped before producing a mature viable seed. Seedless fruit may contain traces of the developing seed and occasionally a seed coat may form and become hard and have the appearance of a seed.

Single gene converted (conversion). "Single gene converted" (or conversion) plant refers to plants which are developed by a plant breeding technique called backcrossing wherein essentially all of the desired morphological and physiological characteristics of an inbred are recovered in addition to the single gene transferred into the inbred via the backcrossing technique or via genetic engineering.

Thick rind. "Thick rind" is inherited in a polygenic fashion (controlled by more than one gene). Thick rind is proportional with the overall fruit diameter (fruit size). A rind thickness of ¾" is acceptable for a 16 pound watermelon; but for a 10 pound watermelon the rind should be of no more than ¼" to be marketable.

Triploid plants. "Triploid plants" means plants or transplants derived from planting triploid seeds or from micro propagation.

Vine length. "Vine length" is the length of the runners (vines) and is measured in inches.

Yield. "Yield" means the total weight in pounds of all watermelon fruit harvested per acre.

DETAILED DESCRIPTION OF THE INVENTION

The present invention relates to a new allele designated "HMBN" in the genus *Citrullus* that is phenotypically expressed in a multibranching compact plant and small fruit. The present invention also relates to a watermelon seed, a watermelon plant and plant parts, a watermelon variety and a watermelon hybrid which comprise the new HMBN allele.

The present invention also relates to a method of producing the disclosed watermelon plants and seeds.

The plant habit of a watermelon having the mutant allele has a noticeable increase in secondary branching compared to normal diploids and to homozygous lines containing the dw-2 or the dw-1 genes.

The allele of the present invention is readily transferred between the deposited cultivar and its related cultivars. The allele and the methods of the present invention can be used to modify and reduce the weight of fruits and the plant habit of all *C. lanatus* cultivars for commercial production. Generally, the methods involve emasculation of one parent, followed by application of pollen from the other parent to the stigma of the first parent. The crosses can be performed using either parent as the pollen parent.

A plant of the present invention can be obtained by crossing a plant homozygous for the claimed mutant allele with any watermelon cultivar lacking the allele. The plant containing the allele can be any *C. lanatus* variety including a cultivar in which the factor has been previously genetically fixed.

Because the HMBN allele acts as a single recessive allele, the $F_1$ generation will not be multibranching. Only a plant homozygous for the allele will fully exhibit the multibranching phenotype. This phenotype can be used to identify progeny that are homozygous for the claimed mutant allele. After selfing the $F_1$ population, the $F_2$ generation will exhibit the phenotype in a ratio of approximately 1:3. Backcrossing $F_2$ multibranched individuals with a recurrent normal parent plant will produce the backcrossed $F_1$ population. Selfing the backcrossed $F_1$ population will give the backcrossed $F_2$ generation. As in the $F_2$ population, the multibranching trait will segregate in a ratio of about 1:3 in this population. Repeated backcrosses will produce a multibranching cultivar with the characteristics of the recurrent parent cultivar. The HMBN allele will thus become genetically fixed in the resulting cultivar. The trait may then be transmitted by sexual crossing to other cultivars if desired.

Other breeding schemes can be used to introduce the HMBN allele into the desired cultivar. The particular scheme used is not critical to the invention, so long as the allele is stably incorporated into the genome of the cultivar. For example, a marker gene can be used. A nucleic acid probe which hybridizes to the marker gene can be used to identify the desired plants in the $F_1$ generation.

In order to determine if an unknown multibranching cultivar possesses the claimed HMBN allele, a classic genetic test for allelism can be performed. The cultivar is crossed with a plant known to possess the claimed allele. By analyzing the resulting $F_1$ generation, the genotype of the unknown cultivar can be determined. If the unknown cultivar possesses the HMBN allele, the multibranching phenotype will be observed in the $F_1$ generation.

The HMBN allele is readily transferred from one cultivar to another. The homozygous condition is fairly easy to identify. The homozygote can be identified early, well before flowering.

The HMBN allele will advantageously be introduced into varieties that contain other desirable genetic traits such as resistance to disease, early fruit maturation, drought tolerance, fruit shape, seedlessness, and the like.

The watermelon of the present invention was an unexpected result that arose from a watermelon breeding project. A watermelon breeding line, known as line 610f5, was used in the breeding project.

The watermelon mutant of the present invention was crossed into other seed lines and into vegetative lines. A series of watermelon plants expressing the mutant trait in the F₂ generation was produced. Self seed from this series of plants yielded plants which were all multibranching.

The invention also relates to methods for producing a watermelon plant containing in its genetic material one or more transgenes and to the transgenic watermelon plant produced by that method.

In another aspect, the present invention provides for single gene converted plants of HMBN. The single transferred gene may preferably be a dominant or recessive allele. Preferably, the single transferred gene will confer a trait such as male sterility, herbicide resistance, insect resistance, resistance for bacterial, fungal, or viral disease, male fertility, early maturity, enhanced nutritional quality, and enhanced flavor. The single gene may be a naturally occurring watermelon gene or a transgene introduced through genetic engineering techniques.

The invention further provides methods for developing watermelon plants in a watermelon plant breeding program using plant breeding techniques including recurrent selection, backcrossing, pedigree breeding, restriction fragment length polymorphism enhanced selection, genetic marker enhanced selection and transformation. Seeds, watermelon plants, and parts thereof produced by such breeding methods are also part of the invention.

This present invention is directed to developing unique plants of the *Citrullus* species. The watermelon plant of the present invention expresses a substantial increase in branching resulting in a compact plant. A transferable gene or allele, designated HMBN, that conveys this characteristic has been isolated and incorporated into other genetic backgrounds. The allele of the instant invention has also been expressed in different genetic backgrounds of watermelon.

EXAMPLES

The following examples are provided to further illustrate the present invention and are not intended to limit the invention beyond the limitations set forth in the appended claims.

Example 1

The HMBN allele of the present invention greatly increases the number of secondary branches per plant. Tested standard diploid varieties averaged 16 secondary branches per plant; tested dwarfs ranged from 3 to 25 secondary branches with an average of 11.3 per plant. The multibranching lines of the present invention ranged from 32 to 72 secondary branches per plant with an average of 44.9. In the instant invention, the plants are visibly smaller than standard diploid varieties. The average longest branch of the present invention is 142.8 cm compared to 226.7 cm of a standard diploid variety. The six different tested dwarf lines averaged 100.6 cm for the longest branch, less than both the multibranching lines of the present invention and the standard diploids. In the present invention, the plants also have noticeably smaller internodes than the standard diploids but not as small as the dwarf lines.

As shown in Table 1 below, a variety containing the HMBN allele of the present invention, HMBN, is compared to two dwarf varieties, J86 (dw-2) and Bush Jubilee (dw-1), and to a standard diploid variety, Allsweet.

TABLE 1

| | Variety | | | |
|---|---|---|---|---|
| Character | HMBN | J86 | Bush Jubilee | Allsweet |
| Ave. longest branch | 142.8 cm | 116 cm | 120.7 cm | 226.7 cm |
| Ave. shortest branch | 55.1 cm | 54.3 cm | 76.3 cm | 124.0 cm |
| Ave. no. primary branches | 6.9 | 5.8 | 5.3 | 4.7 |
| Ave. no. secondary branches at 30 cm | 44.9 | 19.3 | 7.3 | 14.7 |
| Ave. no. secondary branches at 90 cm | 49.3 | 18.3 | 6.3 | 14.7 |
| Ave. length of internodes | 4.4 cm | 3.4 | 4.1 cm | 7.2 cm |

The HMBN allele of the present invention causes a very visible increase in the number of flowers per plant compared to both the tested dwarf lines and the diploid standards. This increase in the number of flowers applies to both male and female flowers and is constant during the flowering period.

In Table 2 below, a variety containing the HMBN allele of the present invention, HMBN, is compared to two dwarf varieties, J86 and Bush Jubilee, and to a standard diploid, Allsweet, for the number of flowers per plant over a 22 day flowering period.

TABLE 2

| Ave. No. of male/female flowers per plant for each variety | | | | |
|---|---|---|---|---|
| | HMBN | J86 | Bush Jubilee | Allsweet |
| Male flowers day 1 | 7 | 3 | 1 | 3 |
| Female flowers day 1 | 1 | 0 | 0 | 0 |
| Male flowers day 8 | 27 | 12 | 6 | 5 |
| Female flowers day 8 | 3 | 1 | 1 | 0 |
| Male flowers day 15 | 19 | 10 | 8 | 3 |
| Female flowers day 15 | 2 | 1 | 2 | 0 |
| Male flowers day 22 | 13 | 17 | 4 | 1 |
| Female flowers day 22 | 1 | 0 | 1 | 0 |

The HMBN allele of the present invention also increases the number of fruit per plant compared to the tested dwarf and standard diploid varieties. The multibranching lines of the present invention average 9.1 fruit per plant whereas the dwarf lines average 1.8 fruit per plant and the standard diploid variety averages 1.0 fruit per plant. The fruit weight of the varieties containing the HMBN allele of the present invention also were smaller than the standard diploids, 1.6 kg compared to 8.98 kg.

In Table 3, a variety containing the HMBN allele of the present invention, HMBN, is compared to two dwarf varieties, J86 and Bush Jubilee, and a standard diploid variety, Allsweet, for leaf and fruit characteristics.

TABLE 3

| | Variety | | | |
|---|---|---|---|---|
| Leaf and fruit characters | HMBN | J86 | Bush Jubilee | Allsweet |
| Ave. leaf width (cm) | 8.7 | 8.8 | 9.8 | 11.3 |
| Ave. leaf length (cm) | 10.0 | 13.0 | 18.3 | 19.7 |
| Ave. fruit number | 9.1 | 2.7 | 1.0 | 1.0 |
| Ave. fruit weight (kg) | 0.87 | 3.7 | 5.6 | 8.98 |

Example 2

The HMBN line and the two dwarf lines, J86 and Bush Jubilee, were crossed to produce all possible $F_1$ combinations. All $F_1$s resulted in normal vine types indicating that the HMBN, dw-1 and dw-2 genes are single recessive genes.

Further Embodiments of the Invention

This invention also is directed to methods for producing a watermelon plant by crossing a first parent watermelon plant with a second parent watermelon plant wherein either the first or second parent watermelon plant contains the HMBN allele of the present invention. Further, this invention also is directed to methods for producing an inbred watermelon line HMBN-derived watermelon plant by crossing an inbred watermelon line containing the HMBN allele with a second watermelon plant and growing the progeny seed, and repeating the crossing and growing steps with the inbred watermelon line HMBN-derived plant from 1, 2, 3, 4, 5, 6 to 7 times. Thus, any such methods using a watermelon line containing the HMBN allele are part of this invention: selfing, backcrosses, hybrid production, crosses to populations, and the like. All plants produced using a watermelon line containing the HMBN allele as a parent are within the scope of this invention, including plants derived from inbred watermelon lines having HMBN.

It should be understood that the inbred could, through routine manipulation of cytoplasmic or other factors, be produced in a male-sterile form. Such embodiments are also contemplated within the scope of the present claims.

As used herein, the term plant includes plant cells, plant protoplasts, plant cell tissue cultures from which watermelon plants can be regenerated, plant calli, plant clumps and plant cells that are intact in plants or parts of plants, such as embryos, pollen, ovules, flowers, leaves, stalks, and the like.

As it is well known in the art, tissue culture of watermelon can be used for the in vitro regeneration of watermelon plants. Tissues cultures of various tissues of watermelon and regeneration of plants therefrom are well known and published. By way of example, a tissue culture comprising organs has been used to produce regenerated plants as described in Regeneration and Micropropagation: Techniques, Systems and Media 1991-1995, in Herman, E. B., ed., *Recent Advances in Plant Tissue Culture*, Volume 3 (1995); Desamero et al., *Plant Cell Tiss. Org. Cult.* 33:265-271 (1993); Tabei et al., *Plant Tiss. Cult. Leff.* 10:235 (1993). Thus, another aspect of this invention is to provide cells which, upon growth and differentiation, produce watermelon plants having the physiological and morphological characteristics of a watermelon line containing the HMBN allele.

With the advent of molecular biological techniques allowing the isolation and characterization of genes that encode specific protein products, scientists in the field of plant biology developed a strong interest in engineering the genome of plants to contain and express foreign genes, or additional or modified versions of native, or endogenous, genes (perhaps driven by different promoters) in order to alter the traits of a plant in a specific manner. Such foreign additional and/or modified genes are referred to herein collectively as "transgenes". Over the last fifteen to twenty years several methods for producing transgenic plants have been developed, and the present invention in particular embodiments also relates to transformed versions of the claimed plants having the mutant allele.

Plant transformation involves the construction of an expression vector which will function in plant cells. Such a vector comprises DNA comprising a gene under control of, or operatively linked to, a regulatory element (for example, a promoter). The expression vector may contain one or more such operably linked gene/regulatory element combinations. The vector(s) may be in the form of a plasmid, and can be used alone or in combination with other plasmids, to provide transformed watermelon plants, using transformation methods as described below to incorporate transgenes into the genetic material of the watermelon plant(s).

Expression Vectors for Watermelon Transformation

Marker Genes—Expression vectors include at least one genetic marker, operably linked to a regulatory element (a promoter, for example) that allows transformed cells containing the marker to be either recovered by negative selection, i.e., inhibiting growth of cells that do not contain the selectable marker gene, or by positive selection, i.e., screening for the product encoded by the genetic marker. Many commonly used selectable marker genes for plant transformation are well known in the transformation arts, and include, for example, genes that code for enzymes that metabolically detoxify a selective chemical agent which may be an antibiotic or an herbicide, or genes that encode an altered target which is insensitive to the inhibitor. A few positive selection methods are also known in the art.

One commonly used selectable marker gene for plant transformation is the neomycin phosphotransferase II (nptII) gene, isolated from transposon Tn5, which, when placed under the control of plant regulatory signals, confers resistance to kanamycin. Fraley et al., *Proc. Natl. Acad. Sci. U.S.A.*, 80:4803 (1983) Eck et al., *Plant Cell Report*, 14:5 299-304 (1995). Another commonly used selectable marker gene is the hygromycin phosphotransferase gene which confers resistance to the antibiotic hygromycin. Vanden Elzen et al., *Plant Mol. Biol.*, 5:299 (1985).

Additional selectable marker genes of bacterial origin that confer resistance to antibiotics include gentamycin acetyl transferase, streptomycin phosphotransferase and aminoglycoside-3'-adenyl transferase, the bleomycin resistance determinant. Hayford et al., *Plant Physiol.* 86:1216 (1988), Jones et al., *Mol. Gen. Genet.*, 210:86 (1987), Svab et al., *Plant Mol. Biol.* 14:197 (1990), Hille et al., *Plant Mol. Biol.* 7:171 (1986). Other selectable marker genes confer resistance to herbicides such as glyphosate, glufosinate or broxynil. Comai et al., *Nature* 317:741-744 (1985), Gordon-Kamm et al., *Plant Cell* 2:603-618 (1990) and Stalker et al., *Science* 242:419-423 (1988).

Selectable marker genes for plant transformation which are not of bacterial origin include, for example, mouse dihydrofolate reductase, plant 5-enol-pyruvyl-shikimate-3-phosphate synthase and plant acetolactate synthase. Eichholtz et al., *Somatic Cell Mol. Genet.* 13:67 (1987), Shah et al., *Science* 233:478 (1986), Charest et al., *Plant Cell Rep.* 8:643 (1990).

Another class of marker genes for plant transformation requires screening of presumptively transformed plant cells rather than direct genetic selection of transformed cells for resistance to a toxic substance such as an antibiotic. These genes are particularly useful to quantify or visualize the spatial pattern of expression of a gene in specific tissues and are frequently referred to as reporter genes because they can be fused to a gene or gene regulatory sequence for the investigation of gene expression. Commonly used genes for screening presumptively transformed cells include beta-glucuronidase (GUS), alpha-galactosidase, luciferase and chloramphenicol acetyltransferase. Jefferson, R. A., *Plant Mol. Biol. Rep.* 5:387 (1987), Teeri et al., *EMBO J.* 8:343 (1989), Koncz et al., *Proc. Natl. Acad. Sci U.S.A.* 84:131 (1987), DeBlock et al., *EMBO J.* 3:1681 (1984), Charng et al., *Plant Science Limerick*. 1994, 98: 2,175-183, Hu Wei e al., *In vitro Cellular and Developmental Biology Plant* 37:1 12-18 (2001), Agharbaoui et al., *Plant Cell Report* 15:1/2 102-105 (1995).

In vivo methods for visualizing GUS activity that do not require destruction of plant tissue are available. Molecular Probes publication 2908, Imagene Green™, p. 1-4(1993) and Naleway et al., *J. Cell Biol.* 115:151a (1991). However, these in vivo methods for visualizing GUS activity have not proven useful for recovery of transformed cells because of low sensitivity, high fluorescent backgrounds and limitations associated with the use of luciferase genes as selectable markers.

A gene encoding Green Fluorescent Protein (GFP) has been utilized as a marker for gene expression in prokaryotic and eukaryotic cells. Chalfie et al., *Science* 263:802 (1994). GFP and mutants of GFP may be used as screenable markers.

Promoters—Genes included in expression vectors must be driven by a nucleotide sequence comprising a regulatory element, for example, a promoter. Several types of promoters are now well known in the transformation arts, as are other regulatory elements that can be used alone or in combination with promoters.

As used herein, "promoter" includes reference to a region of DNA upstream from the start of transcription and involved in recognition and binding of RNA polymerase and other proteins to initiate transcription. A plant promoter is a promoter capable of initiating transcription in plant cells. Examples of promoters under developmental control include promoters that preferentially initiate transcription in certain tissues, such as leaves, roots, seeds, fibers, xylem vessels, tracheids, or sclerenchyma. Such promoters are referred to as "tissue-preferred". Promoters which initiate transcription only in certain tissue are referred to as "tissue-specific". A "cell type" specific promoter primarily drives expression in certain cell types in one or more organs, for example, vascular cells in roots or leaves. An "inducible" promoter is a promoter which is under environmental control. Examples of environmental conditions that may effect transcription by inducible promoters include anaerobic conditions or the presence of light. Tissue-specific, tissue-preferred, cell type specific, and inducible promoters constitute the class of "non-constitutive" promoters. A "constitutive" promoter is a promoter which is active under most environmental conditions.

A. Inducible Promoters

An inducible promoter is operably linked to a gene for expression in watermelon. Optionally, the inducible promoter is operably linked to a nucleotide sequence encoding a signal sequence which is operably linked to a gene for expression in watermelon. With an inducible promoter the rate of transcription increases in response to an inducing agent.

Any inducible promoter can be used in the instant invention. See Ward et al., *Plant Mol. Biol.* 22:361-366 (1993). Exemplary inducible promoters include, but are not limited to, that from the ACEI system which responds to copper (Meft et al., *PNAS* 90:4567-4571 (1993)); In2 gene from maize which responds to benzenesulfonamide herbicide safeners (Hershey et al., *Mol. Gen Genetics* 227:229-237 (1991) and Gatz et al., *Mol. Gen. Genetics* 243:32-38 (1994)) or Tet repressor from Tn10 (Gatz et al., *Mol. Gen.* *Genetics* 227:229-237 (1991)). A particularly preferred inducible promoter is a promoter that responds to an inducing agent to which plants do not normally respond. An exemplary inducible promoter is the inducible promoter from a steroid hormone gene, the transcriptional activity of which is induced by a glucocorticosteroid hormone (Schena et al., *Proc. Natl. Acad. Sci. U.S.A.* 88:0421 (1991)).

B. Constitutive Promoters

A constitutive promoter is operably linked to a gene for expression in watermelon or the constitutive promoter is operably linked to a nucleotide sequence encoding a signal sequence which is operably linked to a gene for expression in watermelon.

Many different constitutive promoters can be utilized in the instant invention. Exemplary constitutive promoters include, but are not limited to, the promoters from plant viruses such as the 35S promoter from CaMV (Odell et al., *Nature* 313:810-812 (1985), Tababeizadeh et al., *Plant Cell Report* 19:2 197-202 (1999), Kunik et al., *Acta Horticulturae* 447, 387-391 (1997)) and the promoters from such genes as rice actin (McElroy et al., *Plant Cell* 2:163-171 (1990)); ubiquitin (Christensen et al., *Plant Mol. Biol.* 12:619-632 (1989) and Christensen et al., *Plant Mol. Biol.* 18:675-689 (1992)); pEMU (Last et al., *Theor. Appl. Genet.* 81:581-588 (1991)); MAS (Velten et al., *EMBO J.* 3:2723-2730 (1984)) and maize H3 histone (Lepetit et al., *Mol. Gen. Genetics* 231:276-285 (1992) and Atanassova et al., *Plant Journal* 2 (3): 291-300 (1992)).

The ALS promoter, Xba1/Ncol fragment, 5' to the *Brassica napus* ALS3 structural gene (or a nucleotide sequence similar to said Xba1/Ncol fragment), represents a particularly useful constitutive promoter. See PCT application WO96/30530.

C. Tissue-Specific or Tissue-Preferred Promoters

A tissue-specific promoter is operably linked to a gene for expression in watermelon. Optionally, the tissue-specific promoter is operably linked to a nucleotide sequence encoding a signal sequence which is operably linked to a gene for expression in watermelon. Plants transformed with a gene of interest operably linked to a tissue-specific promoter produce the protein product of the transgene exclusively, or preferentially, in a specific tissue.

Any tissue-specific or tissue-preferred promoter can be utilized in the instant invention. Exemplary tissue-specific or tissue-preferred promoters include, but are not limited to, a root-preferred promoter, such as that from the phaseolin gene (Murai et al., *Science* 23:476-482 (1983) and Sengupta-Gopalan et al., *Proc. Natl. Acad. Sci. U.S.A.* 82:3320-3324 (1985)), such as the promoter rolD from *Agrobacterium rhizogenes* as mentioned in Grichko et al., *Plant Physiology and Biochemistry* 39:1 19-25 (2001); a leaf-specific and light-induced promoter such as that from cab or rubisco (Simpson et al., *EMBO J.* 4(11):2723-2729 (1985) and Timko et al., *Nature* 318:579-582 (1985)); an anther-specific promoter such as that from LAT52 (Twell et al., *Mol. Gen. Genetics* 217:240-245 (1989)); a pollen-specific promoter such as that from Zm13 (Guerrero et al., *Mol Gen. Genetics* 244:161-168 (1993)) or a microspore-preferred promoter such as that from apg (Twell et al., *Sex. Plant Reprod.* 6:217-224 (1993)). Signal Sequences for Targeting Proteins to Subcellular Compartments Transport of protein produced by transgenes to a subcellular compartment such as the chloroplast, vacuole, peroxisome, glyoxysome, cell wall or mitochondrion or for secretion into the apoplast, is accomplished by means of operably linking the nucleotide sequence encoding a signal sequence to the 5' and/or 3' region of a gene encoding the protein of interest. Targeting sequences at the 5' and/or 3' end of the structural gene may determine, during protein synthesis and processing, where the encoded protein is ultimately compartmentalized.

The presence of a signal sequence directs a polypeptide to either an intracellular organelle or subcellular compartment or for secretion to the apoplast. Many signal sequences are known in the art. See, for example Becker et al., *Plant Mol. Biol.* 20:49 (1992); Close, P. S., Master's Thesis, Iowa State University (1993); Knox, C., et al., *Plant Mol. Biol.* 9:3-17 (1987); Lerner et al., *Plant Physiol.* 91:124-129 (1989); Fontes et al., *Plant Cell* 3:483-496 (1991); Matsuoka et al., *Proc. Natl. Acad. Sci.* 88:834 (1991); Gould et al., *J. Cell. Biol.* 108:1657 (1989); Creissen et al., *Plant J.* 2:129 (1991); Kalderon, et al., *Cell* 39:499-509 (1984); Steifel, et al., *Plant Cell* 2:785-793 (1990).

Foreign Protein Genes and Agronomic Genes

With transgenic plants according to the present invention, a foreign protein can be produced in commercial quantities. Thus, techniques for the selection and propagation of transformed plants, which are well understood in the art, yield a plurality of transgenic plants which are harvested in a conventional manner, and a foreign protein then can be extracted from a tissue of interest or from total biomass. Protein extraction from plant biomass can be accomplished by known methods which are discussed, for example, by Heney and Orr, *Anal. Biochem.* 114:92-6 (1981).

According to a preferred embodiment, the transgenic plant provided for commercial production of foreign protein is watermelon. In another preferred embodiment, the biomass of interest is seed. For the relatively small number of transgenic plants that show higher levels of expression, a genetic map can be generated, primarily via conventional RFLP, PCR and SSR analysis, which identifies the approximate chromosomal location of the integrated DNA molecule. For exemplary methodologies in this regard, see Glick and Thompson, Methods in Plant Molecular Biology and Biotechnology CRC Press, Boca Raton 269:284 (1993). Map information concerning chromosomal location is useful for proprietary protection of a subject transgenic plant. If unauthorized propagation is undertaken and crosses made with other germplasm, the map of the integration region can be compared to similar maps for suspect plants, to determine if the latter have a common parentage with the subject plant. Map comparisons would involve hybridizations, RFLP, PCR, SSR and sequencing, all of which are conventional techniques.

Likewise, by means of the present invention, agronomic genes can be expressed in transformed plants. More particularly, plants can be genetically engineered to express various phenotypes of agronomic interest. Exemplary genes implicated in this regard include, but are not limited to, those categorized below:

1. Genes that Confer Resistance to Pests or Disease and that Encode:

A. Plant disease resistance genes. Plant defenses are often activated by specific interaction between the product of a disease resistance gene (R) in the plant and the product of a corresponding avirulence (Avr) gene in the pathogen. A plant mutant allele can be transformed with cloned resistance gene(s) to engineer plants that are resistant to specific pathogen strains. See, for example Jones et al., *Science* 266:789 (1994) (cloning of the tomato Cf-9 gene for resistance to *Cladosporium fulvum*); Martin et al., *Science* 262: 1432 (1993) (tomato Pto gene for resistance to *Pseudomonas syringae* pv. tomato encodes a protein kinase); Mindrinos et al., *Cell* 78:1089 (1994) (*Arabidopsis* RSP2 gene for resistance to *Pseudomonas syringae*).

B. A *Bacillus thuringiensis* protein, a derivative thereof or a synthetic polypeptide modeled thereon. See, for example, Geiser et al., *Gene* 48:109 (1986), who disclose the cloning and nucleotide sequence of a Bt-δ-endotoxin gene. Moreover, DNA molecules encoding δ-endotoxin genes can be purchased from American Type Culture Collection, Manassas, Va., for example, under ATCC Accession Nos. 40098, 67136, 31995 and 31998. See also Mandaokat et al., *Crop Protection.* 2000, 19: 5, 307-312.

C. A lectin. See, for example, the disclosure by Van Damme et al., *Plant Molec. Biol.* 24:25 (1994), who disclose the nucleotide sequences of several *Clivia miniata* mannose-binding lectin genes.

D. Genes coding for the coat proteins of the Cucumber Mosaic virus (CMV), see Tomassoli et al., *Molecular Breeding.* 1999, 5: 2,121-130, which confers resistance to CMV.

E. An enzyme inhibitor, for example, a protease or proteinase inhibitor or an amylase inhibitor or a polygalacturonase inhibitor protein. See, for example, Abe et al., *J. Biol. Chem.* 262:16793 (1987) (nucleotide sequence of rice cysteine proteinase inhibitor), Huub et al., *Plant Molec. Biol.* 21:985 (1993) (nucleotide sequence of cDNA encoding tobacco proteinase inhibitor 1), Sumitani et al., *Biosci. Biotech. Biochem.* 57:1243 (1993) (nucleotide sequence of *Streptomyces nitrosporeus* α-amylase inhibitor) and Powell et al., *Molecular Plant Microbe Interaction.* 2000, 13: 9 942-950 (tomatoes transformed with pear fruit polygalacturonase inhibitor protein to inhibit fungal pathogen endopolygalacturonase).

F. An insect-specific hormone or pheromone such as an ecdysteroid or juvenile hormone, a variant thereof, a mimetic based thereon, or an antagonist or agonist thereof. See, for example, the disclosure by Hammock et al., *Nature* 344:458 (1990), of baculovirus expression of cloned juvenile hormone esterase, an inactivator of juvenile hormone.

G. An insect-specific peptide or neuropeptide which, upon expression, disrupts the physiology of the affected pest. For example, see the disclosures of Regan, *J. Biol. Chem.* 269:9 (1994) (expression cloning yields DNA coding for insect diuretic hormone receptor), and Pratt et al., *Biochem. Biophys. Res. Comm.* 163:1243 (1989) (an allostatin is identified in *Diploptera puntata*). See also U.S. Pat. No. 5,266,317 to Tomalski et al., who disclose genes encoding insect-specific, paralytic neurotoxins.

H. An insect-specific venom produced in nature by a snake, a wasp, etc. For example, see Pang et al., *Gene* 116:165 (1992), for disclosure of heterologous expression in plants of a gene coding for a scorpion insectotoxic peptide.

I. An enzyme responsible for a hyper-accumulation of a monoterpene, a sesquiterpene, a steroid, a hydroxamic acid, a phenylpropanoid derivative or another non-protein molecule with insecticidal activity.

J. An enzyme involved in the modification, including the post-translational modification, of a biologically active molecule; for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase and a glucanase, whether natural or synthetic. See PCT application WO 93/02197 in the name of Scott et al., which discloses the nucleotide sequence of a callase gene. DNA molecules which contain chitinase-encoding sequences can be obtained, for example, from the ATCC under Accession Nos. 39637 and 67152. See also Kramer et al., *Insect Biochem. Molec. Biol.* 23:691 (1993), who teach the nucleotide sequence of a cDNA encoding tobacco hookworm chitinase, and Kawalleck et al., *Plant Molec. Biol.* 21:673 (1993), who provide the nucleotide sequence of the parsley ubi4-2 polyubiquitin gene.

K. A molecule that stimulates signal transduction. For example, see the disclosure by Botella et al., *Plant Molec. Biol.* 24:757 (1994), of nucleotide sequences for mung bean calmodulin cDNA clones, and Griess et al., *Plant Physiol.* 104:1467 (1994), who provide the nucleotide sequence of a maize calmodulin cDNA clone.

L. A hydrophobic moment peptide. See PCT application WO95/16776 (disclosure of peptide derivatives of Tachyplesin which inhibit fungal plant pathogens) and PCT application WO95/18855 (teaches synthetic antimicrobial peptides that confer disease resistance).

M. A membrane permease, a channel former or a channel blocker. For example, see the disclosure of Jaynes et al., *Plant Sci* 89:43 (1993), of heterologous expression of a cecropin-β lytic peptide analog to render transgenic tobacco plants resistant to *Pseudomonas solanacearum*.

N. A viral-invasive protein or a complex toxin derived therefrom. For example, the accumulation of viral coat proteins in transformed plant cells imparts resistance to viral infection and/or disease development effected by the virus from which the coat protein gene is derived, as well as by related viruses. See Beachy et al., *Ann. Rev. Phytopathol.* 28:451 (1990). Coat protein-mediated resistance has been conferred upon transformed plants against alfalfa mosaic virus, cucumber mosaic virus, tobacco streak virus, potato virus X, potato virus Y, tobacco etch virus, tobacco rattle virus and tobacco mosaic virus.

O. An insect-specific antibody or an immunotoxin derived therefrom. Thus, an antibody targeted to a critical metabolic function in the insect gut would inactivate an affected enzyme, killing the insect. Cf. Taylor et al., Abstract #497, Seventh Int'l Symposium on Molecular Plant-Microbe Interactions (Edinburgh, Scotland) (1994) (enzymatic inactivation in transgenic tobacco via production of single-chain antibody fragments).

P. A virus-specific antibody. See, for example, Tavladoraki et al., *Nature* 366:469 (1993), who show that transgenic plants expressing recombinant antibody genes are protected from virus attack.

Q. A developmental-arrestive protein produced in nature by a pathogen or a parasite. Thus, fungal endo-α-1, 4-D-polygalacturonases facilitate fungal colonization and plant nutrient release by solubilizing plant cell wall homo-a-1,4-D-galacturonase. See Lamb et al., *Bio/Technology* 10:1436 (1992). The cloning and characterization of a gene which encodes a bean endopolygalacturonase-inhibiting protein is described by Toubart et al., *Plant J.* 2:367 (1992).

R. A developmental-arrestive protein produced in nature by a plant. For example, Logemann et al., *Bioi/Technology* 10:305 (1992), have shown that transgenic plants expressing the barley ribosome-inactivating gene have an increased resistance to fungal disease.

2. Genes that Confer Resistance to an Herbicide, for Example:

A. An herbicide that inhibits the growing point or meristem such as an imidazolinone or a sulfonylurea. Exemplary genes in this category code for mutant ALS and AHAS enzyme as described, for example, by Lee et al., *EMBO J.* 7:1241 (1988), and Miki et al., *Theor. Appl. Genet.* 80:449 (1990), respectively.

B. Glyphosate (resistance impaired by mutant 5-enolpyruvylshikimate-3-phosphate synthase (EPSP) and aroA genes, respectively) and other phosphono compounds such as glufosinate (phosphinothricin acetyl transferase (PAT) and *Streptomyces hygroscopicus* PAT, bar, genes), and pyridinoxy or phenoxy propionic acids and cyclohexones (ACCase inhibitor-encoding genes). See, for example, U.S. Pat. No. 4,940,835 to Shah, et al., which discloses the nucleotide sequence of a form of EPSP which can confer glyphosate resistance. A DNA molecule encoding a mutant aroA gene can be obtained under ATCC accession number 39256, and the nucleotide sequence of the mutant gene is disclosed in U.S. Pat. No. 4,769,061 to Comai. European patent application No. 0 333 033 to Kumada et al., and U.S. Pat. No. 4,975,374 to Goodman et al., disclose nucleotide sequences of glutamine synthetase genes which confer resistance to herbicides such as L-phosphinothricin. The nucleotide sequence of a PAT gene is provided in European application No. 0 242 246 to Leemans et al. DeGreef et al., *Bio/Technology* 7:61 (1989), describe the production of transgenic plants that express chimeric bar genes coding for PAT activity. Exemplary of genes conferring resistance to phenoxy propionic acids and cyclohexones, such as sethoxydim and haloxyfop are the Acc1-S1, Acc1-S2 and Acc1-S3 genes described by Marshall et al., *Theor. Appl. Genet.* 83:435 (1992).

C. An herbicide that inhibits photosynthesis, such as a triazine (psbA and gs+genes) or a benzonitrile (nitrilase gene). Przibilla et al., *Plant Cell* 3:169 (1991), describe the transformation of *Chlamydomonas* with plasmids encoding mutant psbA genes. Nucleotide sequences for nitrilase genes are disclosed in U.S. Pat. No. 4,810,648 to Stalker, and DNA molecules containing these genes are available under ATCC Accession Nos. 53435, 67441, and 67442. Cloning and expression of DNA coding for a glutathione S-transferase is described by Hayes et al., *Biochem. J.* 285:173 (1992).

3. Genes that Confer or Contribute to a Value-Added Trait, Such as:

A. Increased flooding tolerance, for example by transforming a plant with a bacterial enzyme ACC deaminase. See Grichko et al., *Plant Physiology and Biochemistry.* 2001. 39: 1,19-25.

B. Improved juice and pulp viscosity, by transforming the plant with an antisense gene of polygalacturonase. For example, see Porretta et al., *Food Chemistry.* 62:283-290 (1998) or Errington et al., *Journal of the Science of Food and Agriculture,* 76:515-519 (1998).

C. Reduced polyethylene production in order to better control the ripening of the fruit by transforming the plant with an S-adenosylmethionine hydrolase. See Good et al., *Plant Molecular Biology.* 1994, 26: 3, 781-790.

D. Obtaining male sterile plants, especially useful in hybrid watermelon production, by introduction of a gene encoding a tobacco PR Glucanase as described in WO9738116.

Methods for Watermelon Transformation

Numerous methods for plant transformation have been developed including biological and physical plant transformation protocols. See, for example, Miki et al., "Procedures for Introducing Foreign DNA into Plants" in *Methods in Plant Molecular Biology and Biotechnology*, Glick B. R. and Thompson, J. E. Eds. (CRC Press, Inc., Boca Raton, 1993) pages 67-88. In addition, expression vectors and in vitro culture methods for plant cell or tissue transformation and regeneration of plants are available. See, for example, Gruber et al., "Vectors for Plant Transformation" in *Methods* in *Plant Molecular Biology and Biotechnology*, Glick B. R. and Thompson, J. E. Eds. (CRC Press, Inc., Boca Raton, 1993) pages 89-119.

A. *Agrobacterium*-Mediated Transformation

One method for introducing an expression vector into plants is based on the natural transformation system of Agrobacterium. See, for example, Frary et al., *Plant Cell Report.* 1996,16: 3/4, 235-240, Roehel et al., *Plant Cell Report.* 1993,12: 11, 644-647, Hu-Wei et al., *In Vitro Cellular and Developmental Biology Plant.* 2001 37: 1,12-18. *A. tumefaciens* and *A. rhizogenes* are plant pathogenic soil bacteria which genetically transform plant cells. The Ti and Ri plasmids of *A. tumefaciens* and *A. rhizogenes*, respectively, carry genes responsible for genetic transformation of the plant. See, for example, Kado, C. I., *Crit. Rev. Plant Sci.* 10:1 (1991). Descriptions of *Agrobacterium* vector systems and methods for *Agrobacterium*-mediated gene transfer are provided by Gruber et al., supra, Miki et al., supra, and Moloney et al., *Plant Cell Reports* 8:238 (1989). See also, U.S. Pat. No. 6.198.022 issued Mar. 6, 2001.

B. Direct Gene Transfer

Despite the fact the host range for *Agrobacterium*-mediated transformation is broad, some major cereal crop and vegetable species and gymnosperms have generally been recalcitrant to this mode of gene transfer, even though some success has recently been achieved in rice and corn. Hiei et al., *The Plant Journal* 6:271-282 (1994) and U.S. Pat. No. 5,591,616 issued Jan. 7, 1997. Several methods of plant transformation collectively referred to as direct gene transfer have been developed as an alternative to *Agrobacterium*-mediated transformation.

A generally applicable method of plant transformation is microprojectile-mediated transformation wherein DNA is carried on the surface of microprojectiles measuring 1 to 4 μm. The expression vector is introduced into plant tissues with a biolistic device that accelerates the microprojectiles to speeds of 300 to 600 m/s which is sufficient to penetrate plant cell walls and membranes. Sanford et al., *Part. Sci. Technol.* 5:27 (1987), Sanford, J. C., *Trends Biotech.* 6:299 (1988), Klein et al., *Bio/Technology* 6:559-563 (1988), Sanford, J. C., *Physiol Plant* 7:206 (1990), Klein et al., *Biotechnology* 10:268 (1992), Baum et al., *Plant Journal.* 1997, 12: 2, 463-469, Eck et al., *Plant Cell Report.* 1995,14: 5, 299-304, Manzara et al., *Plant Molecular Biology Reporter* 123: 221-226 (1994).

Another method for physical delivery of DNA to plants is sonication of target cells. Zhang et al., *Bio/Technology* 9:996 (1991). Alternatively, liposome and spheroplast fusion have been used to introduce expression vectors into plants. Deshayes et al., *EMBO J.,* 4:2731 (1985), Christou et al., *Proc Natl. Acad. Sci. U.S.A.* 84:3962 (1987). Direct uptake of DNA into protoplasts using $CaCl_2$ precipitation, polyvinyl alcohol or poly-L-ornithine has also been reported. Hain et al., *Mol. Gen. Genet.* 199:161 (1985) and Draper et al., *Plant Cell Physiol.* 23:451 (1982). Electroporation of protoplasts and whole cells and tissues has also been described. Donn et al., In Abstracts of VIIth International Congress on Plant Cell and Tissue Culture IAPTC, A2-38, p 53 (1990), D'Halluin et al., *Plant Cell* 4:1495-1505 (1992) and Spencer et al., *Plant Mol. Biol.* 24:51-61 (1994). A transfer of chromosomes has been reported from a transformed donor line of potato to a recipient line of tomato through microprotoplast PEG induced fusion. See Ramalu et al., *Theorical and Applied Genetics* 92:316-325 (1996).

Following transformation of watermelon target tissues, expression of the above-described selectable marker genes allows for preferential selection of transformed cells, tissues and/or plants, using regeneration and selection methods now well known in the art.

The foregoing methods for transformation would typically be used for producing a transgenic plant. The transgenic plant could then be crossed with another (non-transformed or transformed) plant in order to produce a new transgenic plant. Alternatively, a genetic trait which has been engineered into a particular watermelon line using the foregoing transformation techniques could be moved into another line using traditional backcrossing techniques that are well known in the plant breeding arts. For example, a backcrossing approach could be used to move an engineered trait from a public, non-elite variety into an elite variety, or from a variety containing a foreign gene in its genome into a line which does not contain that gene. As used herein, "crossing" can refer to a simple X by Y cross, or the process of backcrossing, depending on the context.

When the term inbred watermelon plant is used in the context of the present invention, this also includes any single gene conversions of that inbred. The term single gene converted plant as used herein refers to those watermelon plants which are developed by a plant breeding technique called backcrossing wherein essentially all of the desired morphological and physiological characteristics of an inbred are recovered in addition to the single gene transferred into the inbred via the backcrossing technique. Backcrossing methods can be used with the present invention to improve or introduce a characteristic into the inbred. The term backcrossing as used herein refers to the repeated crossing of a hybrid progeny back to one of the parental watermelon plants for that inbred. The parental watermelon plant which contributes the gene for the desired characteristic is termed the nonrecurrent or donor parent. This terminology refers to the fact that the nonrecurrent parent is used one time in the backcross protocol and therefore does not recur. The parental watermelon plant to which the gene or genes from the nonrecurrent parent are transferred is known as the recurrent parent as it is used for several rounds in the backcrossing protocol (Poehiman & Sleper, 1994; Fehr, 1987). In a typical backcross protocol, the original inbred of interest (recurrent parent) is crossed to a second inbred (nonrecurrent parent) that carries the single gene of interest to be transferred. The resulting progeny from this cross are then crossed again to the recurrent parent and the process is repeated until a watermelon plant is obtained wherein essentially all of the desired morphological and physiological characteristics of the recurrent parent are recovered in the converted plant, in addition to the single transferred gene from the nonrecurrent parent.

The selection of a suitable recurrent parent is an important step for a successful backcrossing procedure. The goal of a backcross protocol is to alter or substitute a single trait or characteristic in the original inbred. To accomplish this, a single gene of the recurrent inbred is modified or substituted with the desired gene from the nonrecurrent parent, while retaining essentially all of the rest of the desired genetic, and therefore the desired physiological and morphological, constitution of the original inbred. The choice of the particular nonrecurrent parent will depend on the purpose of the backcross; one of the major purposes is to add some commercially desirable and/or agronomically important trait to the plant. The exact backcrossing protocol will depend on the characteristic or trait being altered to determine an appropriate testing protocol. Although backcrossing methods are simplified when the characteristic being transferred is a dominant allele, a recessive allele may also be transferred. In this instance it may be necessary to introduce a test of the progeny to determine if the desired characteristic has been successfully transferred.

Many single gene traits have been identified that are not regularly selected for in the development of a new inbred but that can be improved by backcrossing techniques. Single gene traits may or may not be transgenic; examples of these traits include, but are not limited to, male sterility, such as the PR glucanase gene, herbicide resistance, such as pat or bar genes, resistance for bacterial, fungal (such as I genes used for resistance to *Fusarium oxysporum*), or viral disease (such as genes TM1 and TM2 used for TMV resistance), insect resistance such as Cry1Ac or Mi genes, male fertility, enhanced nutritional quality, enhanced sugar content, enhanced conservation and delayed ripening such as in using nor or rin genes, yield stability and yield enhancement. These genes are generally inherited through the nucleus. Some other known male sterility genes are inherited cytoplasmically, but still act as single gene traits. Several of these single gene traits are described in U.S. Pat. Nos. 5,777,196; 5,948,957 and 5,969,212, the disclosures of which are specifically hereby incorporated by reference.

Deposit Information

Watermelon seeds containing the HMBN mutant allele have been placed on deposit with the American Type Culture Collection (ATCC), 10801 University Boulevard, Manassas, Va. 20110-2209 on Nov. 12, 2004 and having Deposit Accession Number PTA-6300.

Although the foregoing invention has been described in some detail by way of illustration and example for purposes of clarity and understanding. However, it will be obvious that certain changes and modifications such as single gene modifications and somaclonal variants, variant individuals selected from large populations of the plants and the like may be practiced within the scope of the invention, as limited only by the scope of the appended claims.

What is claimed is:

1. A watermelon seed containing an allele designated HMBN wherein a representative sample of seed containing said HMBN allele has been deposited under ATCC Accession No. PTA-6300.

2. The watermelon seed of claim 1, wherein said seed has a pedigree which includes line 610f5 as one of the parental lines.

3. A watermelon seed containing a recessive allele for the multibranching trait designated HMBN, wherein a representative sample of seed containing said HMBN allele has been deposited under ATCC Accession No. PTA-6300.

4. A watermelon plant produced by growing the seed of claim 1.

5. Pollen of the plant of claim 4.

6. An ovule of the plant of claim 4.

7. A tissue culture comprising regenerable cells of the plant of claim 4.

8. A watermelon plant regenerated from said tissue culture of claim 7.

9. A method for producing hybrid watermelon seed comprising crossing a first parent watermelon plant with a second parent watermelon plant and harvesting the resultant hybrid watermelon seed, wherein first or second parent watermelon plant is the watermelon plant of claim 4.

10. A hybrid watermelon plant produced by growing said hybrid watermelon seed of claim 9.

11. A watermelon plant produced by growing the seed of claim 3.

12. Pollen of the plant of claim 11.

13. An ovule of the plant of claim 11.

14. A tissue culture comprising regenerable cells of the plant of claim 11.

15. A watermelon plant regenerated from said tissue culture of claim 14.

16. A method for producing hybrid watermelon seed comprising crossing a first parent watermelon plant with a second parent watermelon plant and harvesting the resultant hybrid watermelon seed, wherein first or second parent watermelon plant is the watermelon plant of claim 11.

* * * * *